United States Patent [19]

Brumfield

[11] Patent Number: 4,554,915
[45] Date of Patent: Nov. 26, 1985

[54] BONE FIXATION FRAME

[75] Inventor: David L. Brumfield, Nesbit, Miss.

[73] Assignee: Richards Medical Company, Memphis, Tenn.

[21] Appl. No.: 473,199

[22] Filed: Mar. 8, 1983

[51] Int. Cl.[4] .............................................. A61F 5/04
[52] U.S. Cl. ................... 128/92 A; 128/92 R
[58] Field of Search ............. 128/92 A, 92 C, 92 R, 128/92 G, 303 R

[56] References Cited

U.S. PATENT DOCUMENTS

| | | | |
|---|---|---|---|
| 1,789,060 | 1/1931 | Wersenbach | 128/92 A |
| 2,238,869 | 4/1941 | Haynes | 128/92 A |
| 2,238,870 | 4/1941 | Haynes | 128/92 A |
| 2,346,346 | 4/1944 | Anderson | 128/92 A |
| 2,702,031 | 2/1955 | Wenger | 128/92 A |
| 3,909,853 | 10/1975 | Lennox | 128/92 C |
| 4,106,128 | 8/1978 | Greenwald et al. | 128/92 C |
| 4,127,119 | 11/1978 | Kronner | 128/92 A |
| 4,135,505 | 1/1979 | Day | 128/92 A |
| 4,299,212 | 11/1981 | Goudfrooy | 128/92 A |
| 4,312,236 | 1/1982 | Danieletto et al. | 128/92 A |

FOREIGN PATENT DOCUMENTS 194247 5/1967 U.S.S.R. .......................... 128/92 R

Primary Examiner—John J. Wilson
Assistant Examiner—C. W. Shedd
Attorney, Agent, or Firm—Pravel, Gambrell, Hewitt & Kimball

[57] ABSTRACT

One external fixation frame, for immobilizing bone segments adjacent a fracture or joint, includes a fixation block with a pair of arms extending from the block across the fracture or joint. Another embodiment has but a single arm while a third embodiment includes one or two arms projecting from each end of the block. A ball and socket joint connects each arm to the block for universal movement thereabout. Length adjustment is accomplished via a turnbuckle formed in each arm. The outer end of each arm includes a slot for connecting to pins inserted in the respective bone segments. Set screws are provided for tightening the ball and socket joints and for holding the pins in the slots.

12 Claims, 12 Drawing Figures

BONE FIXATION FRAME

BACKGROUND OF THE INVENTION

1. Technical Field

The present invention relates to orthopedic external fixation devices and, more particularly, to an improved apparatus for use in orthopedic surgical repairs which is formed of a universally movable and extendable frame that is adjustably secured to skeletal traction pins and then tightened to provide a rigid frame for immobilizing bone sections on either side of a fracture or joint.

2. General Background

Various appliances have been used for the external repair of fractures. This type of repair is generally referred to as external pin fixation and initially involves the surgical insertion of skeletal traction pins on both sides of a fracture or joint to be fused. A frame is connected to the pins for immobilizing the bones and holding them together until the fracture is mended or the joint is fused.

The pins are installed by using a drill to form guide holes in the bone sections. Normally, a template is used for determining the proper location for the holes. However, for many surgical procedures it is difficult to align the pins precisely because of difficult angles and irregular bone shapes. The problem is exacerbated when for some surgical procedures a frame must be connected to pins projecting from opposite sides of a bone. With several pins on each side of the fracture or joint, alignment with pre-formed openings in the frame is often difficult and tends to prolong and complicate the surgery.

Many fixation devices in use today are complex, bulky and difficult to use. There are a number of adjustment points which must be manipulated in order to install the frame. Many frames also have unnecessary parts which add to the difficulty of installation and weight of the device.

SUMMARY OF THE PRESENT INVENTION

The problems discussed above are alleviated by the fixation frame of the present invention which is useful for immobilizing bone sections on opposite sides of a fracture or joint. One embodiment includes a fixation block with a pair of arms extending from it across the fracture or joint. Another embodiment is formed with a single arm. A third embodiment includes one or two arms projecting from each end of the block. The arms are connected to the block through a ball and socket joint which provides universal movement of the arms relative to the block.

Each arm is formed with a turnbuckle for adjusting its length. The outer end of each arm includes a slot which can easily engage surgical pins connected to the bone on one side of the fracture or joint. Set screws are provided for tightening the ball and socket joint and pin slots.

In several embodiments, the block includes a portion which projects from the side opposite the arms that includes a pair of openings with cooperating set screws adapted to engage pins connected to the bone on the opposite side of the fracture or joint. In the embodiment that includes arms projecting from each end of the block, the arms are used to engage the pins.

The foregoing structure provides a frame which is compact with a minimum number of movable parts. The ability of the arms to move universally relative to the block as well as be adjustable lengthwise in a way which is easy to accomplish simplifies the surgeon's job of installing the frame. These features, along with the arms and easily operable set screws, make the arm adaptable to fit on pins which are not precisely aligned. When the two-armed embodiment is used, a precisely aligned, triangular rigid frame is formed when the ends of the arms are tightened on the surgical pins, without the need to connect the arms to each other at their outer ends.

Another advantage of the invention is that for the single arm embodiment, it can, for example, be used to immobilize a fracture near the wrist so that when the arm is loosened the wrist can bend without losing the desired distraction along the fracture. This is possible because the universal joint between the arm and block is located near the wrist joint and adjustable independent of the length adjustment of the arm.

BRIEF DESCRIPTION OF THE DRAWINGS

For a further understanding of the invention, reference should be had to the following detailed description, taken in conjunction with the accompanying drawings, in which.

DETAILED DESCRIPTION OF EXEMPLARY EMBODIMENTS

Figure 1:
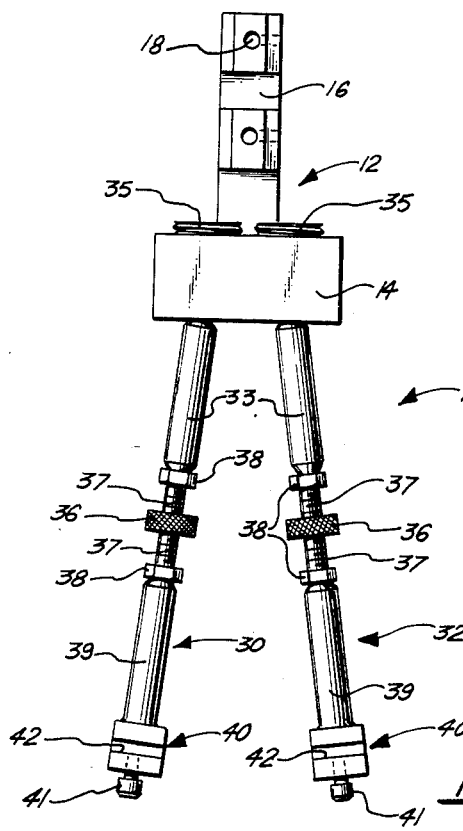
FIG. 1 is a plan view of the two-armed embodiment of the invention.

Referring to FIG. 1, an embodiment of a fixation frame is shown and designated generally by reference numeral 10, which is called a triangular compression device. As described in greater detail below, the device 10 can be used individually or in pairs to form a frame for immobilizing bone sections on opposite sides of a fracture or joint. The device is connected to skeletal traction pins P (see FIGS. 5, 6-10) that are surgically inserted in the bone sections. The device 10 is lightweight and designed with various simply-operated, adjustment features for easy connection to the pins P.

The device 10 includes a fixation block 12 which is formed of a base portion 14 and a clamping portion 16. A pair of spaced apart traction pin openings 18, 20 are formed in the clamping portion 16 which are designed to receive pins P already fixed in a bone section on one side of a fracture or joint. The openings are sized slightly larger than the pins and are provided with laterally intersecting set screws 19, 21 for rigidly connecting the pins P to the block 12.

Figure 2:
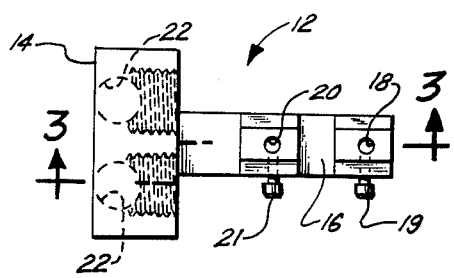
FIG. 2 is a plan view of the fixation block portion of the invention.
Figure 4:
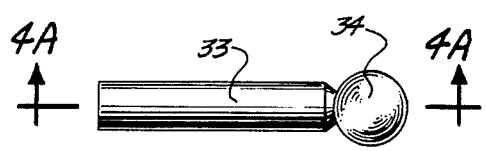
FIGS. 4-4A are plan and sectional views, respectively, of a section of one of the arms of the invention.
Figure 3:
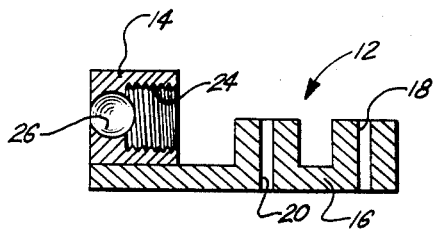
FIG. 3 is a sectional view of the fixation block looking along section line 3—3 in FIG. 3.
Figure 4A:
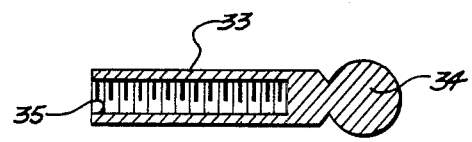

As shown best in FIGS. 2 and 3, a pair of spaced apart socket openings 22 are formed in the base portion 14. Each opening 22 is threaded in part at threaded section 24 and further includes a spherical radius portion 26 for receiving a ball 34 connected at one end of arms 30, 32 on section 33 (see FIG. 4A) for forming ball and socket, universal joints between the block 12 and the arms 30, 32. The openings 22 have radii larger than the ball 34 so that ball and its arm section 33 can be inserted into or removed from the block 12. A spherically radiused set screw 35 is designed to fit in the opening 22 for selectively tightening and loosening the universal joint. During use, the ball and socket joints provide the capability of universal movement to each arm 30, 32 in both rotational and multi-directional, pivotal directions with at least a 20° pivot in each direction away from the longitudinal axis of openings 22.

Each arm 30, 32 includes a turnbuckle for connecting the arm section 33 to another arm section 39. The turnbuckle includes a knurled center wheel 36 connected to oppositely-threaded sections 37 on both sides of the wheel, which are adapted to engage complementary threaded openings formed in the arm sections 33, 39. One such opening in the arm section 33 is designated by reference numeral 35 and shown in FIG. 4A. Lock nuts 38 are provided on the turnbuckle 37 for locking it in place when the arms 30, 32 are at the proper length. The arm sections 39 are equipped with pin clamps 40 which include a slot 42 and a set screw 41 for connecting the arms to skeletal traction pins already set in the bone section on the opposite side of the fracture or joint from the section to which the block 12 is connected.

Figure 5:
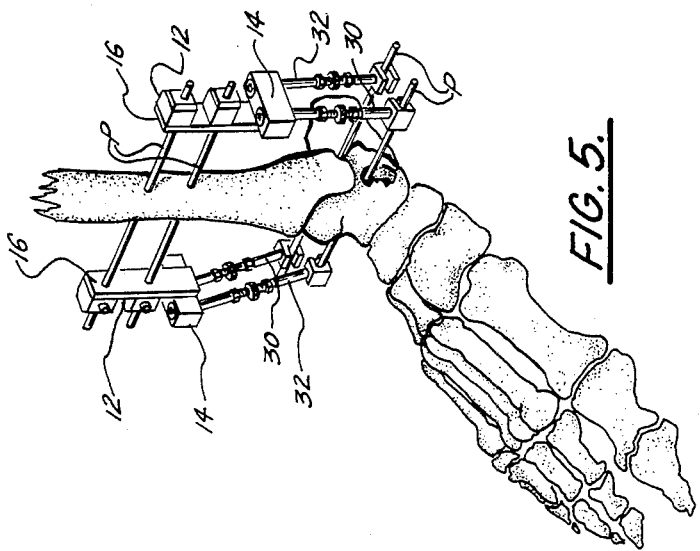
FIG. 5 is a perspective view of the two-armed embodiment of the invention used in an ankle fusion procedure.

One application of the device 10 is shown in FIG. 5 where two of the devices are used in an ankle fusion procedure. Two pins P are inserted by being spaced along the axis of the tibia and another two in the talus generally perpendicular to the other pins. The block 12 on each side of the tibia is then mounted on the pins. The arms 30, 32 are manipulated with the radiused set screws 35, turnbuckle locking nuts 38 and set screws 41, loosened so that the slots 42 can easily fit over the pins P in the tibia. After the devices 12 are in place, all the set screws and locking nuts are tightened for providing a rigid triangular frame on both sides of the ankle for immobilizing the ankle joint.

Figure 9:
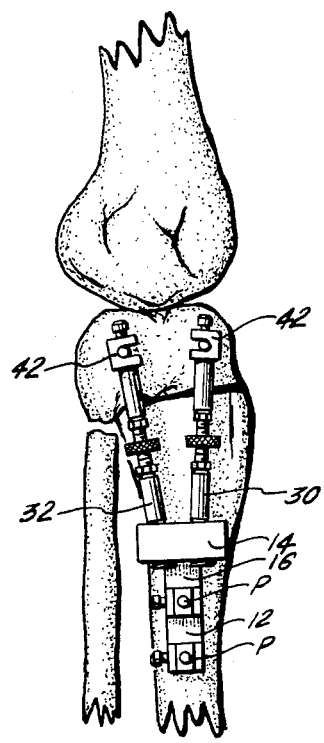
FIGS. 9 and 10 are perspective views of the two-armed embodiment used in a high tibial osteotomy.
Figure 10:
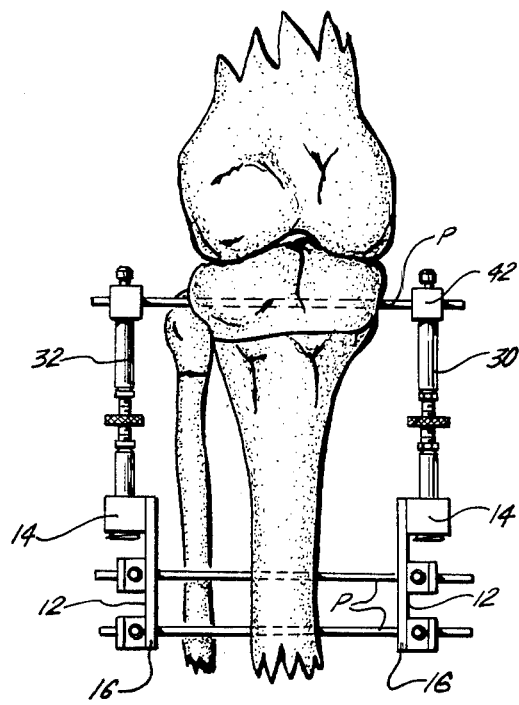

Another application of the invention in which two of the devices 10 are used on opposite sides of the bone is illustrated in FIGS. 9 and 10 where postoperative fixation of a high tibial osteotomy is shown. After surgery, the pins P are inserted in the proximal and distal tibia, the order of which will depend on the surgical procedure used.

After the device is mounted on the pins P in a manner similar to that described above, the turnbuckles are used to obtain compression at the osteotomy site.

Figure 6:
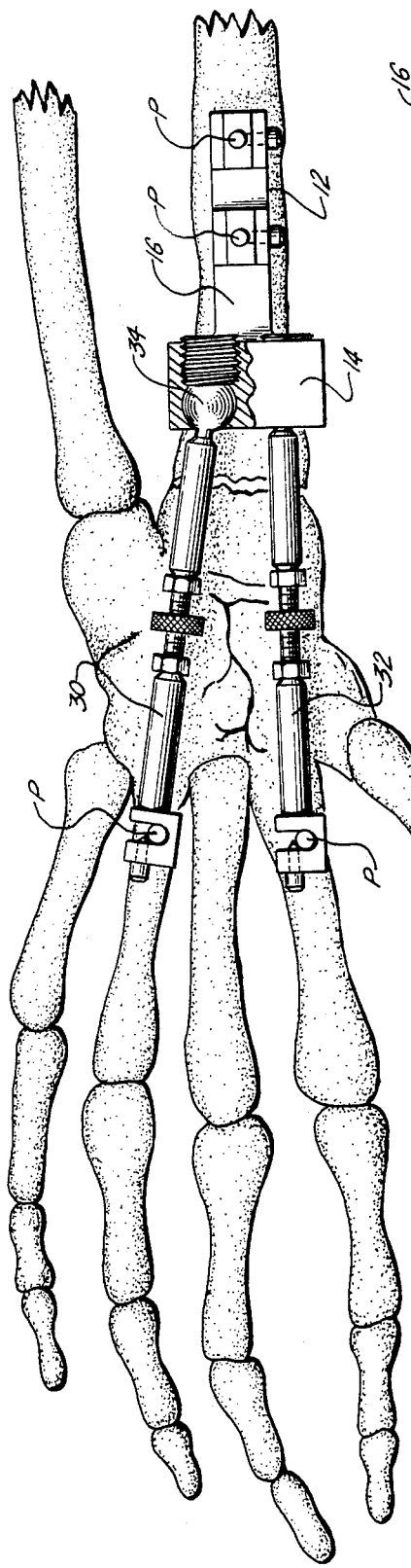
FIG. 6 is a top perspective view of the two-armed embodiment used for forearm repair.

A use of the two-armed embodiment on one side of the immobilized bones is shown in FIG. 6 where the bone sections on opposite sides of a wrist fracture are rigidly held together. The pins P which are connected to two metacarpals are rigidly connected to the arms 30, 32, while pins P connected to a radius are connected to the block 12. After the device 10 is mounted on the pins P, the turnbuckle is used to distract and then correctly align the fractured surfaces, after which the set screws and locking nuts are tightened for immobilizing the joint.

Figure 7:
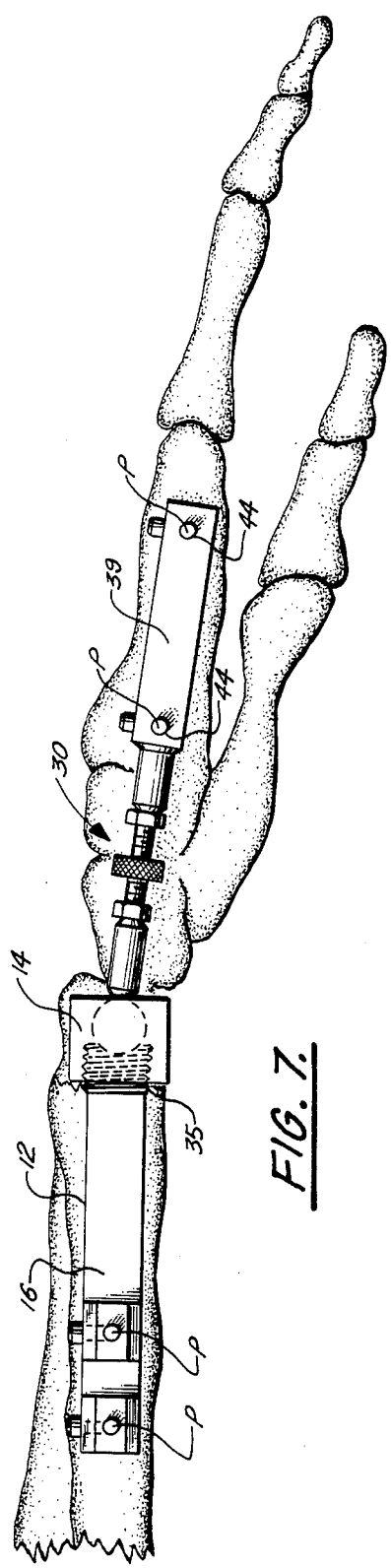
FIGS. 7 and 8 are side and top perspective illustrations, respectively, of the one-armed embodiment of the invention used for immobilizing a broken bone in a forearm.
Figure 8:
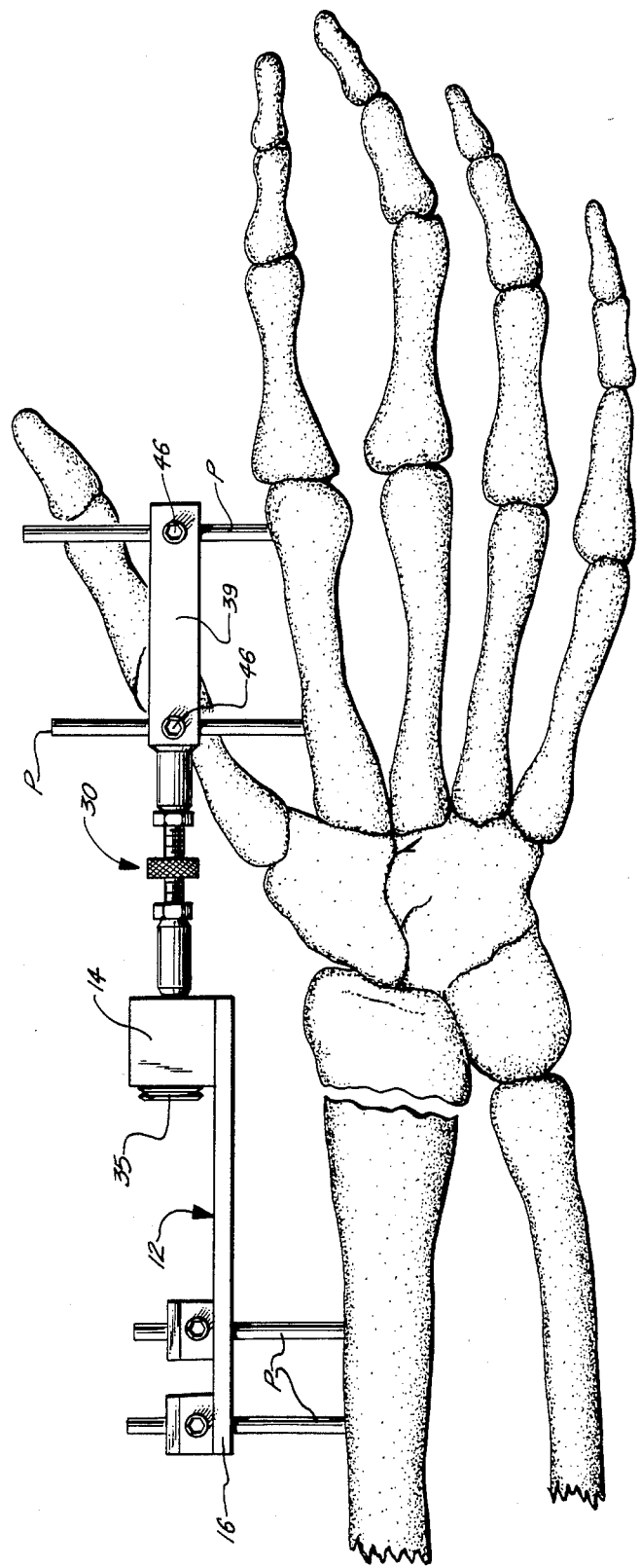

Another embodiment of the invention is shown in FIGS. 7 and 8 where a single arm 30 is connected to the block 12. Otherwise, all the details above in connection with FIGS. 1–4 are the same except that the arm section 39 is formed with two pin openings 44 instead of a single slot as shown above. A set screw 46 is provided to intersect each opening 44 for rigidly connecting the arm to the pins P. An advantage of the invention for this type of fracture is that the universal joint can be located near the wrist joint and the radiused set screw 35 can be loosened to allow the patient to bend and exercise the joint without losing the desired distraction because the locked turnbuckles prevent the arms 30, 32 from varying in length.

The device 10 is mounted on the side of the wrist with connecting pins P located in the forefinger metacarpal and the radius. As with the embodiment shown in FIG. 7, the universal joint formed between the ball 34 and socket opening 22 is located near the joint so that the radiused set screw 35 can be loosened to allow the wrist joint to be bent and exercised without losing the desired distraction.

Figure 11:
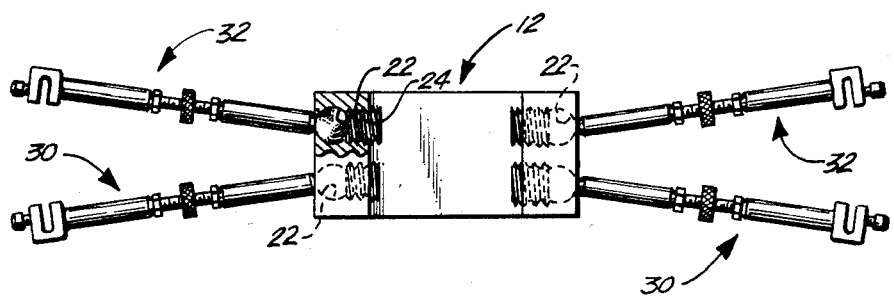
FIG. 11 is a plan view of an embodiment which includes a pair of arms extending from each end of the block.

Another embodiment of the invention is shown generally in FIG. 11 where the block 12 is formed with the socket openings 22 in each end so that a pair of arms 30, 32 are connected at each end of the block 12. This configuration can be used for immobilizing bone sections on opposite sides of a fracture in long bones such as the femur, tibia, etc. Surgical pins (not shown) can be connected, for example, to the bones in an "X" configuration on each side of the fracture, with a pair of the devices connected to the pins for immobilizing the fracture.

Thus, an orthopedic immobilization frame is provided in accordance with the invention which has relative universal movement between parts on opposite sides of a fracture or joint and is longitudinally adjustable. This provides the surgeon with a device that is easily manipulated and can quickly be set. The device has a minimum number if parts, is simple to operate and is relatively small and lightweight.

The embodiments of the invention described above are intended to be merely exemplary and those skilled in the art will be able to make modifications and variations without departing from the spirit and scope of the appended claims.

What is claimed as the present invention is:

1. An orthopedic immobilization device for immobilizing bone sections on opposite sides of a fracture or joint, comprising:
    a. a fixation block;
    b. a pair of arms connected to the block and extending from it for connecting with one of the bone sections;
    c. universal movement means for providing universal movement between one end of the arms and the fixation block;
    d. means for tightening the universal movement means for rigidly connecting the fixation block and arms;
    e. length adjustment means for adjusting the length of the arms;
    f. an open ended slot at the other end of the arms for receiving pins connected to said one bone section;
    g. means for rigidly connecting the pins and arms;
    h. the fixation block including pin receiving means for rigidly connecting the block to a second set of pins connected to another bone section on the other side of the fracture or joint.

2. The orthopedic immobilization device of claim 1 wherein the universal movement means includes a ball and socket joint.

3. The orthopedic immobilization device of claim 2 wherein the universal movement means includes a socket including a threaded opening and a set screw with threads formed to cooperate with the threaded opening for engaging the ball and rigidly connecting the arm to the fixation block.

4. The orthopedic immobilization device of claim 1 wherein the length adjustment means includes a turnbuckle.

5. The orthopedic immobilization device of claim 1 wherein a second pair of arms is connected to the fixation block, the pairs being connected at opposite sides of the block.

6. The orthopedic immobilization device of claim 1 wherein the end of the arm containing the open ended slot is movably mounted with respect to other portions of each arm.

7. The orthopedic immobilization device of claim 1 wherein the pin receiving means includes a pair of spaced openings extending through the fixation block.

8. An orthopedic immobilization frame for rigidly connecting bone sections on opposite sides of a fracture or joint, comprising:
   a. first and second frame sections;
   b. universal movement means for forming a single, multi-directional pivot point adapted for positioning over said joint and connecting the frame sections for allowing selective universal movement between frame sections;
   c. locking means for selectively locking the universal movement means and preventing the universal movement means from moving for providing a rigid connection between the frame sections;
   d. at least the first frame section including length adjustment means for selectively adjusting its length;
   e. pin connecting means for rigidly connecting each frame section to at least one pin connected to one of the bone sections; and
   f. the universal movement means including means for maintaining constant the distance between the pins connected to the respective bone sections when the locking means is not locked, so that an animal joint in the vicinity of the pivot point can be exercised without distraction between the frame sections.

9. The frame of claim 8 wherein the first frame section includes an arm adapted to span the fracture or joint and the universal movement means is connected to the arm.

10. The frame of claim 9 wherein the first frame section includes a pair of arms.

11. The frame of claim 8 wherein the second frame section includes a fixation block.

12. The frame of claim 11 wherein the first frame section includes a pair of arms projecting from one end of the block and further including a second pair of arms projecting from the opposite end of the block and universal movement means between the block and the second pair of arms.

* * * * *